United States Patent
Geertsen (10) Patent No.: US 9,629,575 B2
(45) Date of Patent: Apr. 25, 2017

(54) FILTER DEVICE AND METHOD OF MANUFACTURING A FILTER DEVICE

(71) Applicant: GN Otometrics A/S, Taastrup (DK)

(72) Inventor: Thomas Geertsen, Slagelse (DK)

(73) Assignee: Natus Medical Incorporated, San Carlos, CA (US)

( * ) Notice: Subject to any disclaimer, the term of this patent is extended or adjusted under 35 U.S.C. 154(b) by 173 days.

(21) Appl. No.: 14/590,459

(22) Filed: Jan. 6, 2015

(65) Prior Publication Data
US 2016/0183851 A1  Jun. 30, 2016

(30) Foreign Application Priority Data

Dec. 30, 2014 (DK) .............................. 2014 070838
Dec. 30, 2014 (EP) ..................................... 14200629

(51) Int. Cl.
*H04R 25/00* (2006.01)
*A61B 5/12* (2006.01)
*A61B 5/00* (2006.01)

(52) U.S. Cl.
CPC .............. *A61B 5/123* (2013.01); *A61B 5/121* (2013.01); *A61B 5/6817* (2013.01)

(58) Field of Classification Search
CPC .... H04R 25/00; H04R 25/652; H04R 25/654; H04R 1/1016; H04R 25/65; H04R 1/12; A61B 5/121; A61B 5/123; A61B 5/6817
See application file for complete search history.

(56) References Cited

U.S. PATENT DOCUMENTS

| 4,716,985 A * | 1/1988 | Haertl | H04R 25/65 181/130 |
| 4,828,777 A * | 5/1989 | Birkholz | H04R 25/652 249/175 |
| 4,834,927 A * | 5/1989 | Birkholz | H04R 25/652 249/175 |
| 4,870,689 A * | 9/1989 | Weiss | H04R 25/654 128/867 |

(Continued)

FOREIGN PATENT DOCUMENTS

| DE | 29800758 U1 | 5/1998 |
| EP | 2 393 311 A1 | 7/2011 |

OTHER PUBLICATIONS

Second Technical Examination dated Oct. 13, 2015 for corresponding Danish Patent Application No. PA 2014 70838, 4 pages.

(Continued)

*Primary Examiner* — Matthew Eason
*Assistant Examiner* — Taunya McCarty
(74) *Attorney, Agent, or Firm* — Temmerman Law Office; Mathew J. Temmerman (57) ABSTRACT

A filter device for a hearing test probe and a method of manufacturing a filter device are disclosed. The filter device extends along a center axis in a first direction from a first end to a second end. The filter device comprising: a first part having a first filter structure, a second part having a second filter structure, a first channel extending along the center axis. The first part and second part are joined together, and the first filter structure and the second filter structure define a filter element with a first set of filter openings for the first channel.

11 Claims, 8 Drawing Sheets

(56) References Cited

U.S. PATENT DOCUMENTS

| | | | |
|---|---|---|---|
| 4,879,750 A * | 11/1989 | Nassler | H04R 25/654 |
| | | | 381/325 |
| 5,105,904 A | 4/1992 | Olsen | |
| 5,166,659 A * | 11/1992 | Navarro | H04R 25/654 |
| | | | 181/130 |
| 5,293,008 A * | 3/1994 | Danielsen | H04R 25/654 |
| | | | 181/135 |
| 7,882,928 B2 * | 2/2011 | McMahon | A61B 5/12 |
| | | | 181/135 |
| 2006/0147071 A1 | 7/2006 | Neilson | |
| 2007/0112279 A1 * | 5/2007 | Iseberg | A61B 5/03 |
| | | | 600/559 |
| 2011/0103629 A1 * | 5/2011 | Sjursen | H04R 25/654 |
| | | | 381/325 |
| 2012/0014548 A1 | 1/2012 | van Halteren | |

OTHER PUBLICATIONS

Third Technical Examination—Intention to Grant dated Mar. 18, 2016 for corresponding Danish Patent Application No. PA 2014 70838, 3 pages.
Extended European Search Report dated Jul. 7, 2015 for corresponding European Patent Application No. 14200629.5, 6 pages.
First Technical Examination dated Jun. 16, 2015 for corresponding Danish Patent Application No. PA 2014 70838, 8 pages.

* cited by examiner

FILTER DEVICE AND METHOD OF MANUFACTURING A FILTER DEVICE

RELATED APPLICATION DATA

This application claims priority to and the benefit of Danish Patent Application No. PA 2014 70838 filed on Dec. 30, 2014, pending, and European Patent Application No. 14200629.5 filed on Dec. 30, 2014, pending. The entire disclosures of both of the above applications are expressly incorporated by reference herein.

FIELD

The present disclosure relates to a filter device, e.g. for audiologic test equipment, for preventing cerumen, commonly known as earwax, from entering into a compartment comprising delicate equipment, such as a microphone and/or a speaker. The compartment may be a compartment of a hearing test probe used to perform audiologic tests, such as tympanometric and/or otoacoustic emission tests.

BACKGROUND

In order to perform an audiologic test a probe needs to be inserted into the ear canal of a person to be tested. The probe may hold audio devices, such as a microphone and/or one or more speakers. These components may be damaged or altered by cerumen from the person's ear. Therefore a filter device may be applied to the probe between the components of the probe and the distal end of the probe which is to be inserted into the ear canal.

The filter device needs to enable sound and air to pass through in order for the audiologic tests to be performed. Concurrently the filter needs to stop cerumen from passing into the probe and thereby potentially damaging components of the probe.

Conventional filter devices trap cerumen from the user's ear in order to prevent the cerumen from entering into the probe compartment. However, when cerumen is trapped in the filter, the acoustic properties of the probe may be altered, thereby leading to reduced functionality of the probe.

In a filter device, openings of very small dimensions are desirable. However, it is difficult to carve or pierce a hole in a surface of a desirable small dimension, leading to a high manufacturing cost of the filter device.

SUMMARY

Despite the known solutions there is still a need for a filter device which effectively prevents cerumen from entering into the probe compartment, and a filter device which is easy and inexpensive to manufacture.

Accordingly, a filter device is provided. The filter device extends along a center axis in a first direction from a first end to a second end. The filter device comprises: a first part having a first filter structure; a second part having a second filter structure; and a first channel extending along the center axis. The first part and the second part are joined together, and the first filter structure and the second filter structure define a filter element with a first set of filter openings for the first channel.

Also disclosed is a method for providing and/or manufacturing a filter device, such as a filter device with a first channel. The method comprises: obtaining a first part with a first filter structure; obtaining a second part with a second filter structure; and joining the first part and the second part. Joining the first part and the second part comprises at least partly inserting the first filter structure into the second filter structure to form a filter element with a first set of filter openings for the first channel.

Further disclosed is a first part and/or a second part for a filter device. Further, a hearing test probe comprising a filter device as disclosed herein is provided.

It is an advantage of the present disclosure that a filter device which may be manufactured cheaply by simple processes such as plastic molding is provided. A filter device which lowers manufacturing costs may provide a filter device which may be exchanged after each use and/or after a few uses, and thereby provides for easy usage and highly reliable and consistent measurements.

A filter device for a hearing test probe, the filter device having a first end and a second end, and extending along a center axis in a first direction from the first end to the second end, the filter device includes: a first part having a first filter structure; a second part having a second filter structure; a first channel extending along the center axis; wherein the first part and second part are joined together, and the first filter structure and the second filter structure define a filter element with a first set of filter openings for the first channel.

Optionally, the first filter structure comprises a first primary protruding member having a distal end, and wherein the second filter structure comprises a first primary opening, the first primary protruding member extending at least partly inside the first primary opening along the center axis to form a primary first filter opening of the first set of filter openings.

Optionally, the first primary protruding member has a circular, oval, oblong, triangular, or rectangular cross-section.

Optionally, the first primary protruding member comprises one or more support points including a first support point, and wherein the first support point contacts a first inner sidewall of the first primary opening of the second filter structure.

Optionally, the first filter structure comprises a first secondary protruding member, and wherein the second filter structure comprises a first secondary opening, the first secondary protruding member extending at least partly inside the first secondary opening along the center axis to form a secondary first filter opening of the first set of filter openings.

Optionally, the second part comprises a first coupling part for coupling the first channel to a probe channel, the first coupling part comprising a coupling ridge extending in the first direction and enclosing the first primary opening.

Optionally, a cross-sectional area of the first primary protruding member decreases towards the distal end of the first primary protruding member.

Optionally, the filter device further includes a second channel extending along the center axis, wherein the filter element has a second set of filter openings for the second channel.

Optionally, the first part comprises a tube part with a cavity, and the second part comprises a channel separator extending inside the cavity along the center axis to form the first channel and the second channel.

Optionally, the first filter structure comprises a first primary protruding member and a second primary protruding member; and wherein the second filter structure comprises a first primary opening and a second primary opening; wherein the first primary protruding member extends at least partly inside the first primary opening along the center axis to form a primary first filter opening of the first set of filter openings; and wherein the second primary protruding member extends at least partly inside the second primary opening along the center axis to form a primary second filter opening of the second set of filter openings.

Optionally, the first part and/or the second part is at least partly coated with a hydrophobic substance.

A hearing test probe has the filter device according to any of the embodiments described herein.

A method of manufacturing a filter device with a first channel, includes: obtaining a first part with a first filter structure; obtaining a second part with a second filter structure; and joining the first part and the second part, wherein the act of joining the first part and the second part comprises at least partly inserting the first filter structure into the second filter structure to form a filter element with a first set of filter openings for the first channel.

Optionally, the act of obtaining the first part with the first filter structure comprises plastic molding the first part.

Optionally, the act of joining comprises ultrasonic welding the first part and the second part.

Other features, embodiments, and advantageous will be described below in the detailed description.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The filter device comprises a first channel extending along the center axis. The filter element has a first set of filter openings for the first channel. Additionally or alternatively, the filter device may comprise a second channel extending along the center axis. The filter element may have a second set of filter openings for the second channel. The first set of filter openings may provide fluid communication between the first channel and the surroundings. The second set of filter openings may provide fluid communication between the second channel and the surroundings.

The filter device may comprise a plurality of channels including the first channel, the second channel and/or a third channel extending along the center axis. The channel(s) may at least partly be formed by the first part and/or the second part.

The filter device may have dimensions such that the filter device or part of the filter device may be inserted into a human ear. The filter device may have a length along the center axis, e.g a length less than 15 cm, such as between 0.5 cm and 10 cm, such as between 1 cm and 5 cm, such between 1.5 cm and 3 cm.

The filter element may have a plurality of sets of filter openings for the plurality of channels. The plurality of sets of filter openings for the plurality of channels may include the first set of filter openings for the first channel and the second set of filter openings for the second channel. The filter element may include a third set of filter openings for a third channel. The filter element may include a fourth set of filter openings for a fourth channel. A set of filter openings may comprise one, two, three, four, five six, seven or more filter openings, e.g. in the range from one to ten filter openings.

A filter opening, such as a filter opening of a set of filter openings, may have a cross-sectional shape in a plane perpendicular to the center axis. The cross-sectional shape may be a slit, such as a slit resembling the perimeter or part of a perimeter of a geometrical shape, such as a circle, a rectangle, or an oval. The slit may have a width less than 0.5 mm, such as less than 0.35 mm, such as less than 0.2 mm, such as less than 0.15 mm, such as less than 0.1 mm. The slit may have a constant width and/or a varying width.

The filter device, e.g. the first part, may comprise a tube part with a cavity. The tube part may form outer wall part of one or more channels. The tube part may at least partly enclose the channel(s). The tube part may extend along the center axis. The tube part may have a length less than 10 cm, such as between 0.1 cm and 7 cm, such as between 0.5 cm and 5 cm, such between 1 cm and 3 cm. The tube part may have a circular cross section and/or the tube part may have an oval cross section, and/or the tube part may have a polygonal cross section, and/or the tube part may have a rectangular cross section. The tube part may have a cross-sectional dimension, e.g. a cross-sectional dimension in a plane with a normal parallel to the center axis, such as a diameter and/or a width. The cross-sectional dimension may be selected such that the tube part may be inserted into a human ear canal. The cross-sectional dimension may be less than 2 cm, such as between 0.1 cm and 1.5 cm, such as between 0.2 cm and 1 cm, such as between 0.3 cm and 0.8 cm, such as 0.5 cm.

The filter device, e.g. the second part, may comprise a channel separator extending inside the cavity along the center axis to form the plurality of channels, such as the first channel and the second channel. The channel separator may have a length substantially similar to the length of the tube part. The channel separator may have a length shorter than the length of the tube part, such as 0.1 cm shorter than the length of the tube part. The channel separator may have a length less than 10 cm, such as between 0.1 cm and 7 cm, such as between 0.5 cm and 5 cm, such between 1 cm and 3 cm.

The channel separator may form one or more inner walls, including a first inner wall and/or a second inner wall. The one or more inner walls may radially extend from an intersection, e.g. an intersection extending along the center axis. The channel separator may form four inner walls radially extending from an intersection of the four inner walls extending along the center axis.

One or more inner walls of the channel separator, such as the first inner wall and/or the second inner wall, may have a width in a direction perpendicular to the center axis. The width may be selected such that the one or more inner walls radially extend to an inner side of the cavity of the tube part. The width of one or more inner walls may be less than 10 mm, such as between 1 mm and 8 mm, such as between 2 mm and 6 mm, such as 3 mm.

The first filter structure may comprise a protruding member and/or a plurality of protruding members, such as a first primary protruding member, a first secondary protruding member, a second primary protruding member, and/or a second secondary protruding member. The protruding member(s) may extend along the center axis.

The protruding member and/or the plurality of protruding members, such as the first primary protruding member, the first secondary protruding member, the second primary protruding member, and/or the second secondary protruding member, may have a distal end.

The protruding member and/or the plurality of protruding members, such as the first primary protruding member, the first secondary protruding member, the second primary protruding member, and/or the second secondary protruding member, may have a length parallel to the center axis between 0.1 and 10 mm, such as between 0.5 mm and 8 mm, such as 1 mm 3 mm or 5 mm.

The second filter structure may comprise an opening and/or a plurality of openings, such as first opening(s) and second opening(s), the first opening(s) e.g. including a first primary opening and/or a first secondary opening, and the second opening(s) e.g. including a second primary opening and/or a second secondary opening. The second filter structure may comprise third opening(s) and fourth opening(s), the third opening(s) e.g. including a third primary opening and/or a third secondary opening, and the fourth opening(s) e.g. including a fourth primary opening and/or a fourth secondary opening.

A protruding member may extend at least partly inside (e.g. overlap of at least 0.5 mm along the center axis) or through an opening of the second filter structure along the center axis to form a filter opening of a set of filter openings. For example, the first primary protruding member may extend at least partly inside or through the first primary opening along the center axis, e.g. with an overlap of at least 0.5 mm, to form a primary first filter opening of the first set of filter openings. Alternatively or additionally, the first secondary protruding member may extend at least partly inside or through the first secondary opening along the center axis, e.g. with an overlap of at least 0.5 mm) to form a secondary first filter opening of the first set of filter openings. Alternatively or additionally, the second primary protruding member may extend inside or through the second primary opening along the center axis to form a primary second filter opening of the second set of filter openings. Alternatively or additionally, the second secondary protruding member may extend inside or through the second secondary opening along the center axis to form a secondary second filter opening of the second set of filter openings. Third protruding member(s) may extend at least partly inside or through third opening(s) of the second filter element along the center axis to form third filter opening(s) of the third set of filter openings. Fourth protruding member(s) may extend at least partly inside or through fourth opening(s) of the second filter element along the center axis to form fourth filter opening(s) of the fourth set of filter openings. A plurality of protruding members may extend into or share the same filter opening.

A protruding member and/or a plurality of protruding members, such as the first primary protruding member, the first secondary protruding member, the second primary protruding member, and/or the second secondary protruding member, may have a circular, oval, oblong, triangular, and/or rectangular cross-section. One or more protruding members with an oblong cross-section may be preferred due to size requirements and acoustic properties.

The cross sectional area of a protruding member and/or the plurality of protruding members may decrease towards the distal end of the protruding member. For example, the cross-sectional area of the first primary protruding member may decrease towards the distal end of the first primary protruding member. This may facilitate moulding of the filter structure and/or simplify moulding tools.

The cross-section of the protruding member and/or the plurality of protruding members may be in a plane having a normal parallel to the center axis.

The opening and/or the plurality of openings, such as the first primary opening, the first secondary opening, the second primary opening, and/or the second secondary opening, may have a circular, oval, oblong, triangular, and/or rectangular cross-section. One or more openings with an oblong or oval cross-section may be preferred due to size requirements and acoustic properties.

The cross-section of the opening and/or the plurality of openings may be in a plane having a normal parallel to the center axis.

An opening, such as an opening of the plurality of openings, such as the first primary opening, the first secondary opening, the second primary opening, and/or the second secondary opening, may have a cross-sectional area. The cross-sectional area of an opening may be selected to allow one or more protruding members to extend inside the opening. For example, the cross-sectional area of an opening may be less than 30 $mm^2$, such as between 1 $mm^2$ and 20 $mm^2$, such as between 2 $mm^2$ and 15 $mm^2$.

The protruding member and/or the plurality of protruding members, such as the first primary protruding member, the first secondary protruding member, the second primary protruding member, and/or the second secondary protruding member, may comprise one or more support points, such as a first support point and/or a second support point. The one or more support points may when assembled contact an inner sidewall of the opening in the second filter structure. For example, the first support point of the first primary protruding member may contact a first inner sidewall of the first primary opening in the second filter structure when the filter device is assembled.

Providing support points may provide enhanced precision of the filter opening size, reducing variation in acoustic properties. Furthermore, support points may allow for subsequent fusing of the first part and the second part, e.g. by ultrasonic welding.

The second part may comprise a coupling part and/or a plurality of coupling parts, such as a first coupling part and/or a second coupling part, for coupling a channel, such as the first channel and/or the second channel, to a probe channel. The coupling part and/or the plurality of coupling parts may comprise a coupling ridge extending in the first direction and enclosing the opening and/or the plurality of openings, such as the first primary opening, the first secondary opening, the second primary opening, and/or the second secondary opening. For example, the first coupling part may comprise a coupling ridge extending in the first direction and enclosing the first primary opening and/or the first secondary opening. Alternatively and/or additionally, the second coupling part may comprise a coupling ridge extending in the first direction and enclosing the second primary opening and/or the second secondary opening.

The first part and/or the second part may be at least partly coated with a hydrophobic substance. For example, the first filter structure and/or the second filter structure may be at least partly coated with a hydrophobic substance. For example, inside surfaces of the filter openings may be coated with a hydrophobic substance, e.g. the protruding member and/or the plurality of protruding members and/or the opening and/or the plurality of openings may be at least partly coated with a hydrophobic substance.

Coating a surface with a hydrophobic substance will provide cerumen to be attracted to the surface, thus at least partly trapping the cerumen inside the filter openings, preventing or at least reducing the risk of cerumen from moving through and out of the filter openings.

The first part and/or the second part may be at least partly coated with a hydrophilic substance. For example, the first filter structure and/or the second filter structure may be at least partly coated with a hydrophilic substance. For example, the second end may be coated with a hydrophilic substance, e.g. the protruding member and/or the plurality of protruding members and/or the opening and/or the plurality of openings may be at least partly coated with a hydrophilic substance. Coating a surface with a hydrophilic substance will provide cerumen to be repelled from the surface, thus at least partly preventing cerumen from moving into the filter openings.

The length and width of the filter openings may be varied by varying the layout of the first and second filter structures. For example, the sizes of the protruding member and/or plurality of protruding members of the first filter structure, and/or the sizes of the opening and/or plurality of openings of the second filter structure.

For example, the length of the filter openings may be increased, e.g. by increasing the length of the protruding member and/or plurality of protruding members and/or by increasing the length of the opening and/or plurality of openings, thereby enhancing the prevention of cerumen from advancing through the filter openings.

Alternatively or additionally, the width of the filter openings may be decreased, e.g. by increasing the width of the protruding member and/or plurality of protruding members and/or by decreasing the width of the opening and/or plurality of openings, thereby enhancing the prevention of cerumen from moving into the filter openings.

The width and length of the filter openings may alternatively or additionally be varied to achieve desirable acoustic properties of the filter device.

The first part and/or the second part may be made from plastic, such as acrylonitrile butadiene styrene (ABS), a polycarbonate and acrylonitrile butadiene styrene blend (PC-ABS), and/or polyoxymethylene (POM). Obtaining the first part with the first filter structure and/or the second part with the second filter structure may comprise plastic molding of the first part and/or second part, respectively.

Joining the first part and the second part may comprise ultrasonic welding of the first part and the second part. The first part and/or the second part may comprise energy directors for ultrasonic welding of the first part and the second part. An energy director may be a small protrusion in a surface, such as a cone shaped protrusion.

The filter device may be a first filter device and/or a second filter device of a system of filter devices. The system of filter devices may comprise a plurality of filter devices, e.g. including the first filter device and the second filter device. An intermediate space may be provided between the first filter device and the second filter device. The intermediate space may be provided to trap cerumen between the first filter device and the second filter device.

Throughout, the same reference numerals are used for identical or corresponding parts.

Figure 1:
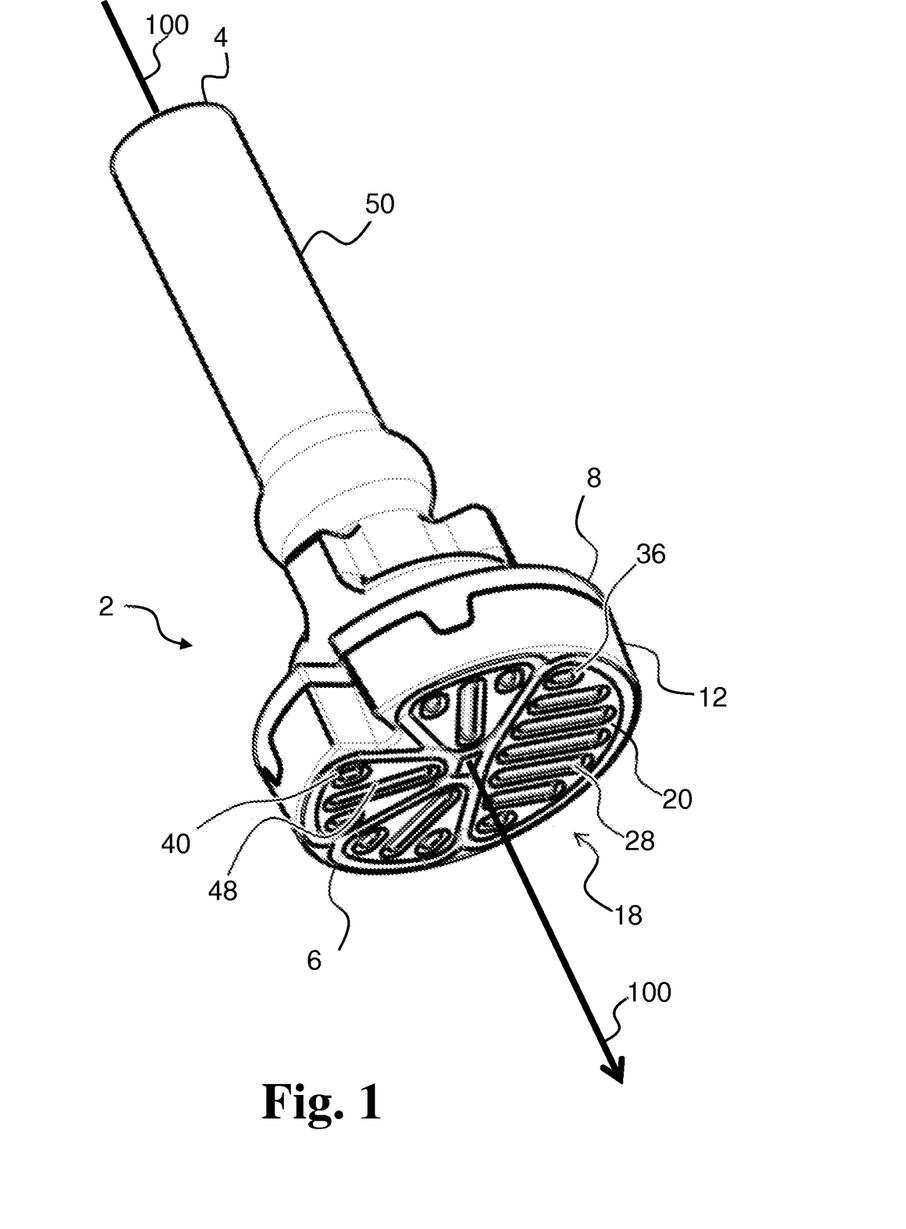
FIG. 1 illustrates an exemplary filter device.

FIG. 1 illustrates an exemplary filter device 2 for a hearing test probe (not shown). The filter device 2 extends along a center axis 100 in a first direction from a first end 4 to a second end 6. The filter device 2 comprises a first part 8 and a second part 12. The filter device comprises a first channel extending along the center axis 100. The first part 8 comprises a tube part 50, wherein the first channel is extending.

The first part 8 has a first filter structure, and the second 12 has a second filter structure. The first part 8 and the second part 12 are joined together, and the first filter structure and the second filter structure define a filter element 18 with a first set of filter openings 20 for a first channel. The first set of filter openings 20 comprises a plurality of first filter openings. The first set of filter openings 20 comprises a primary first filter opening 28 and a secondary first filter opening 36.

The filter element 18 further comprises a second set of filter openings 40 for a second channel. The second set of filter openings 40 comprises a plurality of second filter openings. The second set of filter openings 40 comprises a primary second filter opening 48. The second channel is extending inside the tube part 50.

The filter element 18 may comprise a plurality of sets of filter openings for a plurality of channels. The filter element 18 as illustrated comprises four sets of filter openings for four channels. A plurality of sets of filter openings for a plurality of channels may provide sets of filter openings and channels for different purposes. For example, the first set of filter openings 20 may be intended for outcoming sound, e.g. connected to a speaker, and the second set of filter openings 40 may be intended for incoming sound, e.g. connected to a microphone, and a third set of filter openings may be intended for pressurizing, e.g. connected to a pump.

In an exemplary filter device (not shown), the second part 12 may comprise one or more coupling parts for coupling a channel to a probe channel, e.g. the second part 12 may comprise a first coupling part for coupling the first channel to a probe channel and/or the second part 12 may comprise a second coupling part for coupling the second channel to a probe channel. The first coupling part may comprise a coupling ridge extending in the first direction and enclosing the primary first filter opening 28 and/or the secondary first filter opening 36, such as enclosing the first set of filter openings 20. The second coupling part may comprise a coupling ridge extending in the first direction and enclosing the primary second filter opening 48, such as enclosing the second set of filter openings 40.

Figure 2:
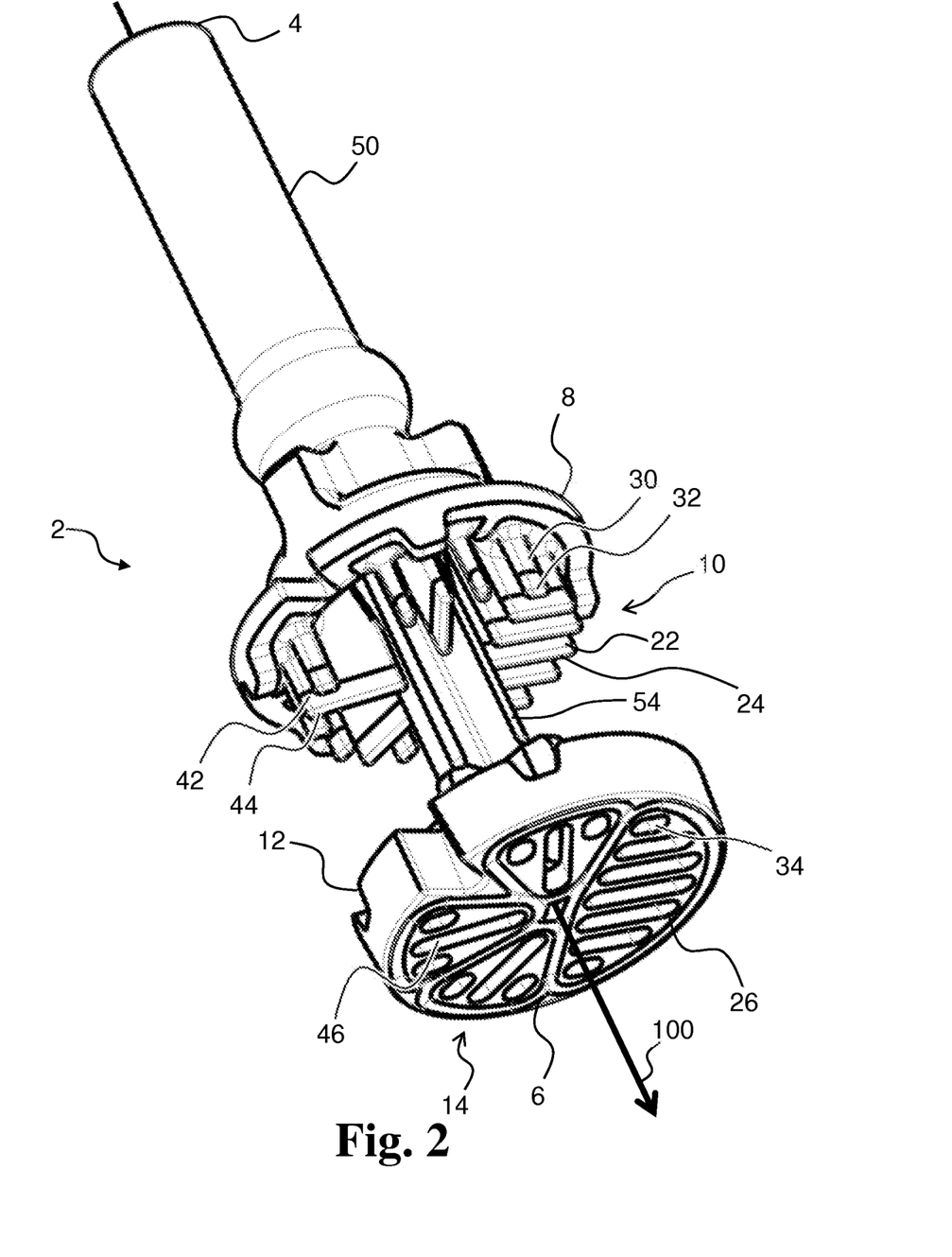
FIG. 2 illustrates a first part and a second part of an exemplary filter device.

FIG. 2 illustrates an exemplary filter device 2 prior to joining the first part 8 and the second part 12 to form the filter device 2 as illustrated in FIG. 1. The filter device 2 comprises the first part 8 having a first filter structure 10 and the second part 12 having a second filter structure 14.

The first part 8 comprises a tube part 50 with a cavity, and the second part 12 comprises a channel separator 54 with four inner walls extending inside the cavity along the center axis 100. The inner walls of the channel separator 54 extending inside the cavity form four channels including a first channel and a second channel.

The first filter structure 10 comprises a first primary protruding member 22 having a distal end 24. The second filter structure comprises a first primary opening 26. After joining the first part 8 and the second part 12, the first primary protruding member 22 extends at least partly inside or through the first primary opening 26 along the center axis to form a primary first filter opening of the first set of filter openings for the first channel as illustrated in FIG. 1.

The first filter structure 10 comprises a plurality of protruding members, and the second filter structure 14 comprises a plurality of openings.

The first filter structure 10 comprises a first secondary protruding member 30 having a distal end 32. The second filter structure comprises a first secondary opening 34. After joining the first part 8 and the second part 12, the first secondary protruding member 30 extends at least partly inside or through the first secondary opening 34 along the center axis to form a secondary first filter opening of the first set of filter openings for the first channel as illustrated in FIG. 1.

The first filter structure 10 comprises a second primary protruding member 42 having a distal end 44. The second filter structure comprises a second primary opening 46. After joining the first part 8 and the second part 12, the second primary protruding member 42 extends at least partly inside or through the second primary opening 46 along the center axis to form a primary second filter opening of the second set of filter openings for the second channel as illustrated in FIG. 1.

After joining the first part 8 and the second part 12, the protruding members of the first filter structure 10, such as the first primary protruding member 22, the first secondary protruding member 30, and/or the second primary protruding member 42 are configured to overlap along the center axis with their respective openings of the second filter structure, such as the first primary opening 26, the first secondary opening 34, and/or the second primary opening 46.

In an exemplary filter device (not shown), the second part 12 may comprise one or more coupling parts for coupling a channel to a probe channel, e.g. the second part 12 may comprise a first coupling part for coupling the first channel to a probe channel and/or the second part 12 may comprise a second coupling part for coupling the second channel to a probe channel. The first coupling part may comprise a coupling ridge extending in the first direction and enclosing the first primary opening 26 and/or the first secondary opening 34. The second coupling part may comprise a coupling ridge extending in the first direction and enclosing the second primary opening 46.

Figure 3:
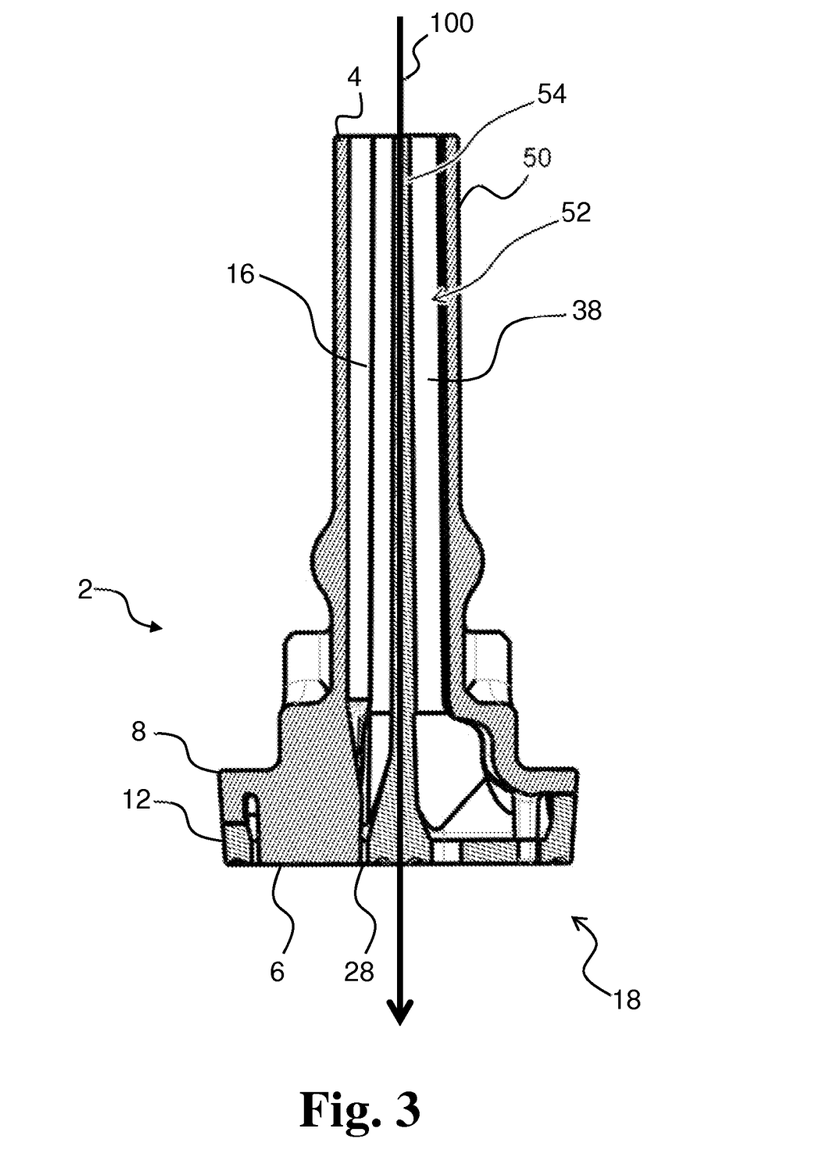
FIG. 3 illustrates a cross section of an exemplary filter device.

FIG. 3 illustrates a cross section of an exemplary filter device 2. The filter device 2 comprises a first channel 16 and a second channel 38. FIG. 3 furthermore illustrates the first part 8 comprising a tube part 50 having a cavity 52, and the second part 12 comprising a channel separator 54 extending inside the cavity 52 along the center axis 100. The channel separator 54 extending inside the cavity 52 forms the first channel 16 and the second channel 38. The first part 8 and the second part 12 are joined together to form a filter element 18 comprising a plurality of filter openings. The filter element 18 comprises a primary first filter opening 28 for the first channel 16. The primary first filter opening 28 may be part of a first set of filter openings for the first channel 16 as described in relation to FIG. 1.

Figure 4A:
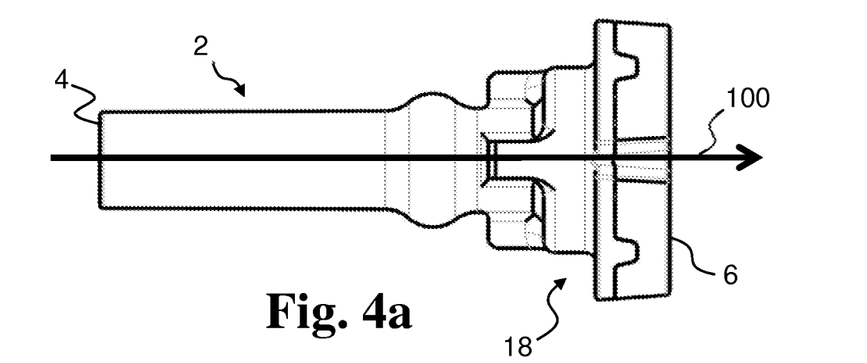
FIG. 4a is a side view of an exemplary filter device.
Figure 4B:
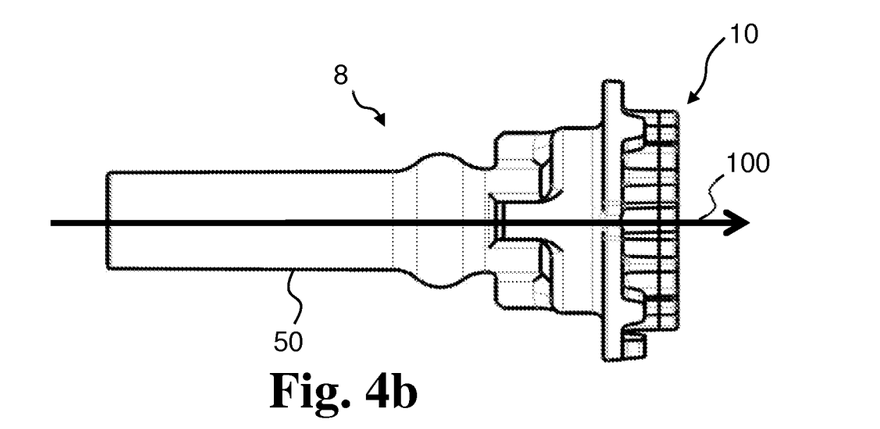
FIG. 4b is a side view of a first part of an exemplary filter device.
Figure 4C:
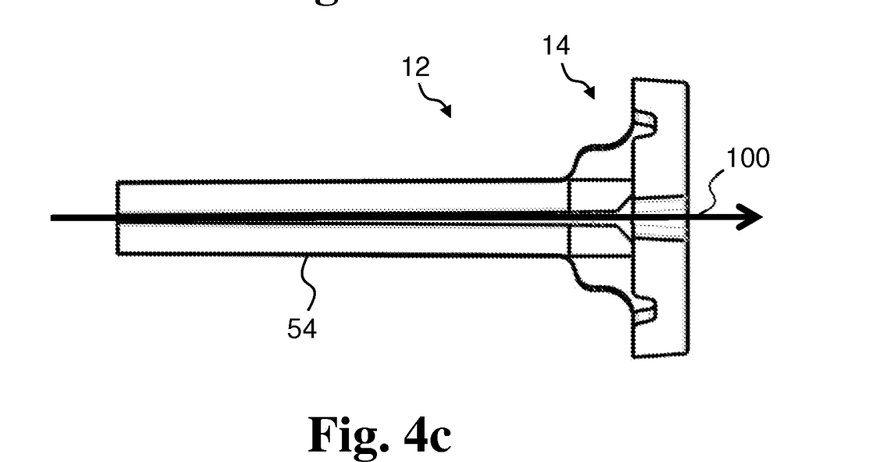
FIG. 4c is a side view of a second part of an exemplary filter device.

FIGS. 4a-4c are side views of an exemplary filter device 2, an exemplary first part 8, and an exemplary second part 12, respectively. FIG. 4a illustrates the filter device 2. FIG. 4b illustrates the first part 8 of the filter device 2. The first part 8 having a first filter structure 10. FIG. 4c illustrates the second part 12 of the filter device 2. The second part having a second filter structure 14. FIG. 4a illustrates the filter device 2 wherein the first part 8 and the second part 12 are joined together. Thereby, the first filter structure 10 and the second filter 14 structure define a filter element 18 of the filter device 2.

Also illustrated in FIGS. 4a-4c are that the first part 8 comprises a tube part 50, and the second part 12 comprises a channel separator 54. After joining the first part 8 and the second part 12, the channel separator 54 extends inside a cavity of the tube part 50 along the center axis 100, forming a first channel and a second channel. Optionally, the channel separator 54 may comprise a plurality of separator walls to form a plurality of channels, e.g. the channel separator 54 may comprise four separator walls to form a first channel, a second channel, a third channel, and a fourth channel.

Figure 5A:
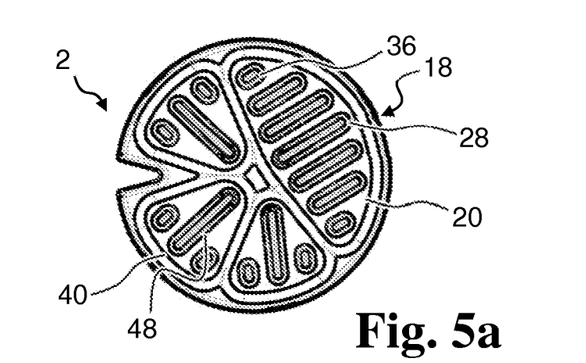
FIG. 5a is an end view of an exemplary filter device.
Figure 5B:
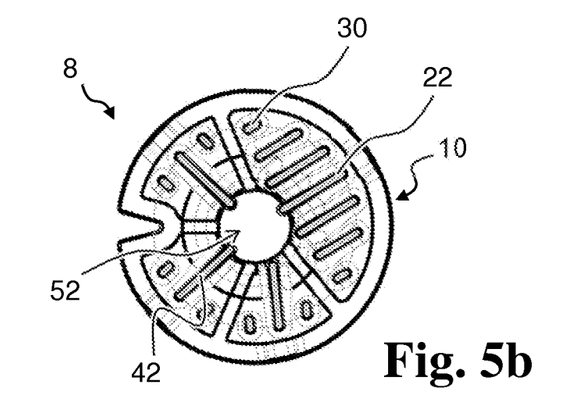
FIG. 5b is an end view of a first part of an exemplary filter device.
Figure 5C:
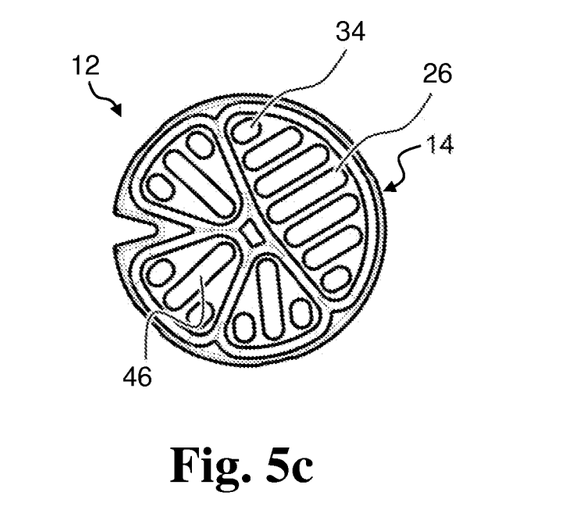
FIG. 5c is an end view of a second part of an exemplary filter device.

FIGS. 5a-5c illustrates an exemplary filter device 2, an exemplary first part 8, and an exemplary second part 12, respectively, shown from the second end 6 (FIG. 1).

FIG. 5a illustrates the filter device 2, wherein the filter element 18 comprises a first set of filter openings 20 for a first channel and a second set of filter openings 40 for a second channel. The first set of filter openings 20 comprises a primary first filter opening 28 and a secondary first filter opening 36. The second set of filter openings 40 comprises a primary second filter opening 48.

FIG. 5b illustrates the first part 8 of the filter device 2. The first part 8 having a first filter structure 10. The first filter structure 10 comprises a plurality of protruding members, including a first primary protruding member 22, a first secondary protruding member 30, and a second primary protruding member 42. Also shown is the cavity 52 of a tube part of the first part 8. As shown in FIG. 5b, a protruding member, such as the first primary protruding member 22, the first secondary protruding member 30, and/or the second primary protruding member 42, may have an oval or oblong cross-section. Alternatively, a protruding member, such as the first primary protruding member 22, the first secondary protruding member 30, and/or the second primary protruding member 42, may be circular, triangular and/or rectangular cross-section.

FIG. 5c illustrates the second part 12 of the filter device 2. The second part having a second filter structure 14. The second filter structure 14 comprises a plurality of openings, including a first primary opening 26, a first secondary opening 34, and a second primary opening 46.

The openings of the second filter structure 14, such as the first primary opening 26, the first secondary opening 34, and/or the second primary opening 46 are slightly bigger than their respective protruding member of the first filter structure 10, such as the first primary protruding member 22, the first secondary protruding member 30, and/or the second primary protruding member 42, e.g. an opening 26, 34, 46 has a cross-sectional area slightly bigger than its respective protruding member 22, 30, 42.

Figure 9:
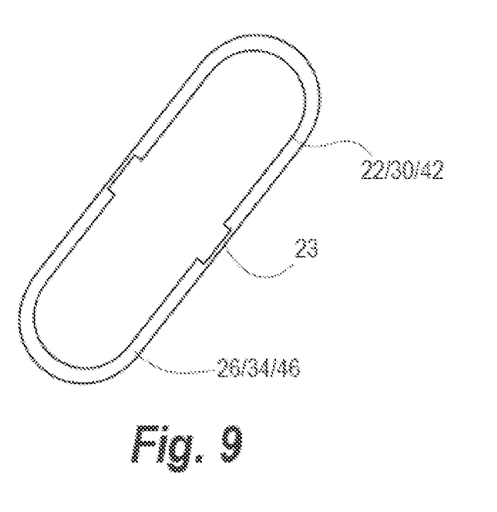
FIG. 9 is an end view of another exemplary filter device.

In some exemplary filter devices (an example of which is shown in FIG. 9) a protruding member of the first filter structure 10, such as the first primary protruding member 22, the first secondary protruding member 30, and/or the second primary protruding member 42, may comprise one or more support points including a first support point 23. After joining the first part 8 and the second part 12, the first support point may contact a first inner sidewall of an opening of the second filter structure 14, such as the first primary opening 26, the first secondary opening 34, and/or the second primary opening 46.

After joining the first part 8 and the second part 12 the first filter structure 10 and the second filter structure 12 defines the filter element 18, as shown in FIG. 5a. After joining the first part 8 and the second part 12, the first primary protruding member 22 extends at least partly inside or through the first primary opening 26 to form the primary first filter opening 28. After joining the first part 8 and the second part 12, the first secondary protruding member 30 extends at least partly inside or through the first secondary opening 34 to form the secondary first filter opening 36. After joining the first part 8 and the second part 12, the second primary protruding member 42 extends at least partly inside or through the second primary opening 46 to form the primary second filter opening 48.

Figure 6A:
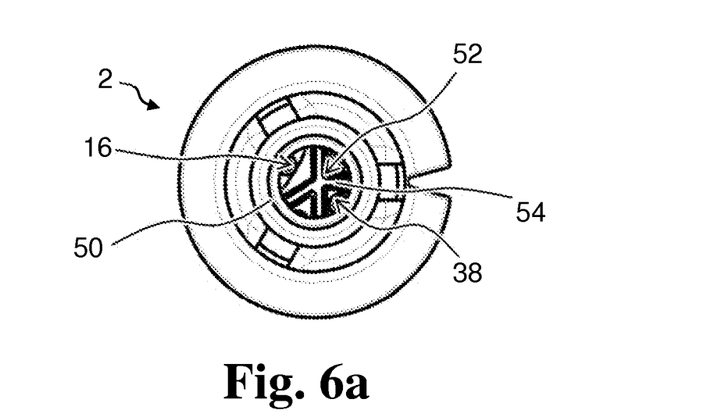
FIG. 6a is an end view of an exemplary filter device.
Figure 6B:
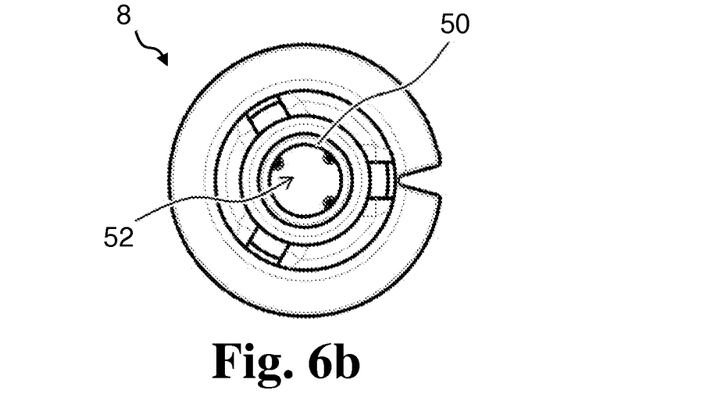
FIG. 6b is an end view of a first part of an exemplary filter device.
Figure 6C:
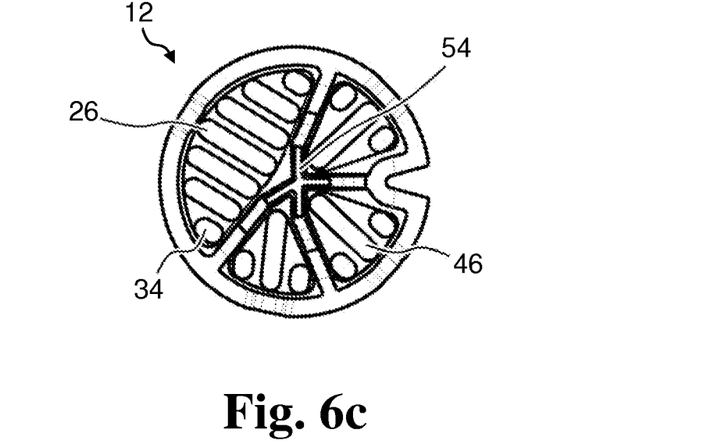
FIG. 6c is an end view of a second part of an exemplary filter device.

FIGS. 6a-6c illustrates an exemplary filter device 2, an exemplary first part 8, and an exemplary second part 12, respectively, shown from the first end 4 (FIG. 1).

FIG. 6a illustrates the filter device 2 comprising a first channel 16 and a second channel 38. FIG. 6b illustrates the first part 8 of the filter device 2. The first part 8 comprises a tube part 50 with a cavity 52. FIG. 6c illustrates the second part 12 of the filter device 2. The second part 12 comprises a channel separator 54. After joining the first part 8 and the second part 12, the filter device 2 comprises a plurality of channels including the first channel 16 and a second channel 38, as shown in FIG. 6a. The first channel 16 and the second channel 38 are separated by the channel separator 54 extending inside the cavity 52 of the tube part 50.

Figure 7:
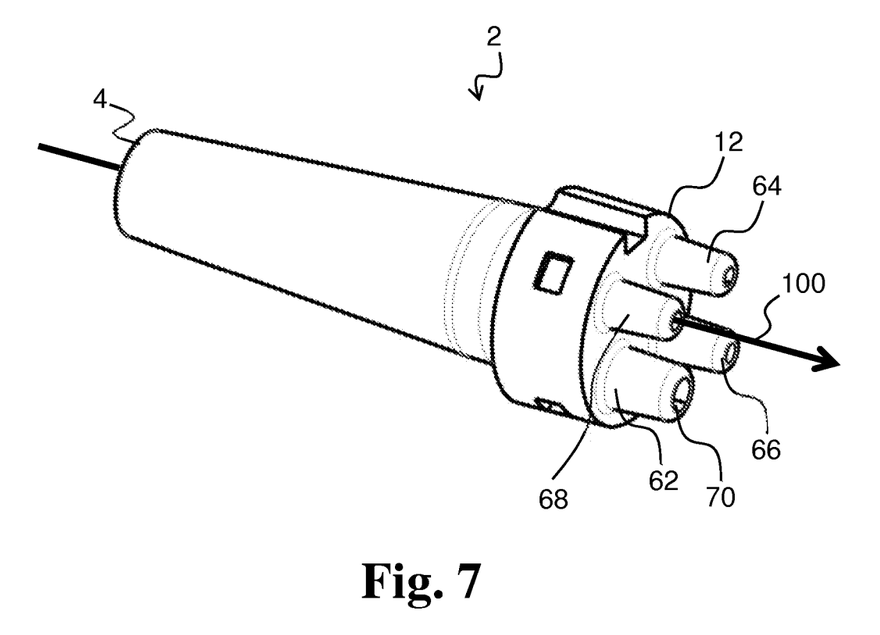
FIG. 7 illustrates an exemplary filter device with a coupling part.

FIG. 7 illustrates an exemplary filter device 2, wherein the second part 12 comprises one or more coupling parts including a first coupling part 62. The second part 12 comprises a plurality of coupling parts including the first coupling part 62, a second coupling part 64, a third coupling part 66 and a fourth coupling part 68, for coupling respective channels and filter openings to respective probes/probe channels. The filter device may comprise a coupling member including the coupling part(s). The coupling member may be a separate member, e.g. made in a material different from the first and second parts. The first coupling part is configured for coupling the first channel to a probe channel and/or for coupling the filter device 2 to a probe. The plurality of coupling parts may be configured for coupling the plurality of channels of the filter device to a plurality of channels of the probe. A coupling part may comprise a coupling ridge extending in the first direction. The first coupling part 62 comprises a first coupling ridge 70 extending in the first direction.

Figure 8:
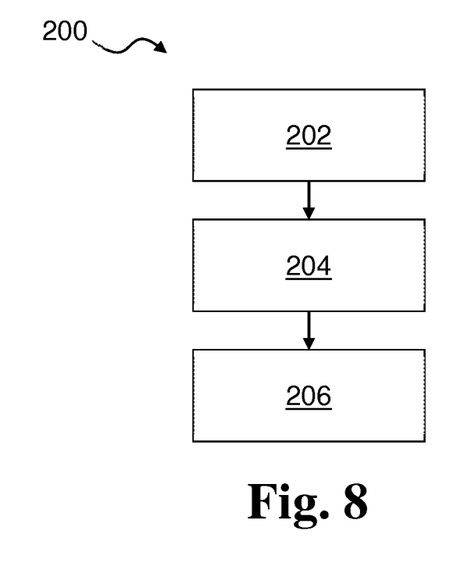
FIG. 8 is a flow diagram of an exemplary method of manufacturing a filter device.

FIG. 8 is a flow diagram of an exemplary method 100 of manufacturing a filter device with a first channel. The method 100 comprises obtaining 102 a first part with a first filter structure, obtaining 104 a second part with a second filter structure, and joining 104 the first part and the second part.

Joining 104 the first part and the second part comprises at least partly inserting the first filter structure into the second filter structure to form a filter element with a first set of filter openings for the first channel.

Obtaining 102 the first part may comprise plastic molding of the first part and/or obtaining 104 the second part may comprise plastic molding of the second part.

Joining 104 the first part and the second part may comprise ultrasonic welding of the first part and the second part. For example, joining 104 the first part and the second part may comprise inserting the first filter structure into the second filter structure, and subsequently ultrasonic welding the first part and the second part.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 2 filter device
4 first end
6 second end
8 first part
10 first filter structure
12 second part
14 second filter structure
16 first channel
18 filter element
20 first set of filter openings
22 first primary protruding member
24 distal end
26 first primary opening
28 primary first filter opening
30 first secondary protruding member
32 distal end
34 first secondary opening
36 secondary first filter opening
38 second channel
40 second set of filter openings
42 second primary protruding member
44 distal end
46 second primary opening
48 primary second filter opening
50 tube part
52 cavity
54 channel separator
62 first coupling part
64 second coupling part
66 third coupling part
68 fourth coupling part
70 coupling ridge
100 center axis
200 method of manufacturing a filter device
202 obtaining a first part
204 obtaining a second part
206 joining the first part and the second part

The invention claimed is:

1. A filter device for a hearing test probe, the filter device allowing sound and air to pass therethrough while preventing ear wax from reaching a component of the hearing test probe, the filter device comprising:
    a first end configured for insertion into an ear canal;
    a second end, wherein the filter device extends along a center axis in a first direction from the first end to the second end;
    a first part having a first filter structure;
    a second part having a second filter structure;
    a first channel corresponding with the center axis;
    wherein the first part and second part are coupled together, and the first filter structure and the second filter structure define a filter element with a first set of filter openings for the first channel; and
    wherein the first filter structure comprises a first primary protruding member having a distal end, and wherein the second filter structure comprises a first primary opening, and wherein the first primary opening has a cross-sectional dimension that is larger than a cross-sectional dimension of the first primary protruding member, allowing the first primary protruding member to be placed at least partly inside the first primary opening to form a primary first filter opening of the first set of filter openings, the primary first filter opening having a first space formed between at least a portion of the first primary protruding member and the first primary opening.

2. The filter device according to claim 1, wherein the first primary protruding member has a circular, oval, oblong, triangular, or rectangular cross-section.

3. The filter device according to claim 1, wherein the first primary protruding member comprises one or more support points including a first support point, and wherein the first support point contacts a first inner sidewall of the first primary opening of the second filter structure.

4. The filter device according to claim 1, wherein the first filter structure comprises a first secondary protruding member, wherein the second filter structure comprises a first secondary opening, and wherein the first secondary opening has a cross-sectional dimension that is larger than a cross-sectional dimension of the first secondary protruding member, allowing the first secondary protruding member to be placed at least partly inside the first secondary opening to form a secondary first filter opening of the first set of filter openings, the secondary first filter opening having a second space formed between at least a portion of the first secondary protruding member and the first secondary opening.

5. The filter device according to claim 1, wherein the second part comprises a first coupling part for coupling the first channel to a probe channel, the first coupling part comprising a coupling ridge extending in the first direction and enclosing the first primary opening.

6. The filter device according to claim 1, wherein a cross-sectional area of the first primary protruding member decreases towards the distal end of the first primary protruding member.

7. The filter device according to claim 1, further comprising a second channel corresponding with the center axis, wherein the filter element has a second set of filter openings for the second channel.

8. The filter device according to claim 1, wherein the first part comprises a tube part and a cavity in the tube part, wherein the tube part forms an outer wall part of one or more channels that includes the first channel, and wherein the second part comprises a channel separator extending inside the cavity along the center axis to form the first channel.

9. The filter device according to claim 7, wherein the first filter structure comprises a second primary protruding member; and
    wherein the second filter structure comprises a second primary opening; and
    wherein the second primary opening has a cross-sectional dimension that is larger than a cross-sectional dimension of the second primary protruding member, allowing the second primary protruding member to be placed at least partly inside the second primary opening to form a primary second filter opening of the second set of filter openings.

10. The filter device according to claim 1, wherein the first part and/or the second part is at least partly coated with a hydrophobic substance.

11. A hearing test probe comprising the filter device according to claim 1.

* * * * *